United States Patent
Marx et al.

(10) Patent No.: US 9,816,156 B2
(45) Date of Patent: Nov. 14, 2017

(54) METHOD OF MANUFACTURING NON-CARRIER-ADDED HIGH-PURITY $^{177}$LU COMPOUNDS AS WELL AS NON-CARRIER-ADDED $^{177}$LU COMPOUNDS

(75) Inventors: Sebastian Marx, Freising (DE); Mark Harfensteller, Unterschleißheim (DE); Konstantin Zhernosekov, München (DE); Tuomo Nikula, Ottobrunn (DE)

(73) Assignee: ITM Isotopen Technologien München AG, Garching (DE)

( * ) Notice: Subject to any disclaimer, the term of this patent is extended or adjusted under 35 U.S.C. 154(b) by 706 days.

(21) Appl. No.: 14/232,205

(22) PCT Filed: Apr. 12, 2012

(86) PCT No.: PCT/EP2012/056644
§ 371 (c)(1),
(2), (4) Date: Mar. 10, 2014

(87) PCT Pub. No.: WO2013/010686
PCT Pub. Date: Jan. 24, 2013

(65) Prior Publication Data
US 2014/0294700 A1 Oct. 2, 2014

(30) Foreign Application Priority Data
Jul. 15, 2011 (DE) .................. 10 2011 051 868

(51) Int. Cl.
*C22B 59/00* (2006.01)
*B01D 15/16* (2006.01)
*B01D 15/18* (2006.01)
*B01D 15/36* (2006.01)
*G21G 1/00* (2006.01)
*A61K 33/24* (2006.01)

(52) U.S. Cl.
CPC .............. *C22B 59/00* (2013.01); *A61K 33/24* (2013.01); *B01D 15/166* (2013.01); *B01D 15/1871* (2013.01); *B01D 15/362* (2013.01); *G21G 1/001* (2013.01); *G21G 2001/0094* (2013.01)

(58) Field of Classification Search
CPC ...... C22B 59/00; A61K 33/24; B01D 15/166; B01D 15/362; B01D 15/1871; G21G 1/001
USPC ............................................ 423/2
See application file for complete search history.

(56) References Cited

U.S. PATENT DOCUMENTS

| | | | |
|---|---|---|---|
| 2,925,431 A | 2/1960 | Choppin et al. | |
| 3,228,750 A | 1/1966 | Lindstrom et al. | |
| 6,716,353 B1 | 4/2004 | Mirzadeh et al. | |
| 2004/0032923 A1 | 2/2004 | Mirzadeh et al. | |
| 2007/0297554 A1 | 12/2007 | Lavie et al. | |

FOREIGN PATENT DOCUMENTS

| | | |
|---|---|---|
| CN | 1131200 | 9/1996 |
| CN | 1796608 | 7/2006 |
| JP | 2010223827 | 10/2010 |
| WO | 2010/054168 | * 5/2010 |

OTHER PUBLICATIONS

Hashimoto et al. "Production of no-carrier-added 177Lu via the 176Yb(n,γ)177Yb→177Lu" (2003) Journal of Radioanalytical and Nucleal Chemistry 255(3): 575-579.

* cited by examiner

*Primary Examiner* — Steven Bos
(74) *Attorney, Agent, or Firm* — Lewis Kohn & Walker LLP; David M. Kohn; Kari Moyer-Henry (57) ABSTRACT

The present invention relates to a column chromatographic method of manufacturing non-carrier-added high-purity $^{177}$Lu compounds for medicinal purposes. In the method in accordance with the invention a cation exchanger and a suitable chelating agent are used. With the method in accordance with the invention it is possible for the first time to provide non-carrier-added high-purity $^{177}$Lu compounds in milligram amounts for pharmaceutical-medicinal purposes from $^{176}$Yb compounds irradiated with thermal neutrons, the radionuclides $^{177}$Lu and $^{176}$Yb being present in an approximate mass ratio of $1:10^2$ to $1:10^{10}$ for purification.

11 Claims, 4 Drawing Sheets

METHOD OF MANUFACTURING NON-CARRIER-ADDED HIGH-PURITY $^{177}$LU COMPOUNDS AS WELL AS NON-CARRIER-ADDED $^{177}$LU COMPOUNDS

This application is a United States National Stage application claiming the benefit of priority under 35 U.S.C. 371 from International Patent Application No. PCT/EP2012/056644 filed Apr. 12, 2012, which claims the benefit of priority from German Patent Application Ser. No. DE 10 2011 051 868.1 filed Jul. 15, 2011, the entire contents of which are herein incorporated by reference.

The present invention relates to a method of manufacturing essentially non-carrier-added high-purity $^{177}$Lu compounds for medicinal purposes and/or diagnostic purposes from $^{176}$Yb compounds irradiated with thermal neutrons, wherein the end products of neutron irradiation, which essentially contain a mixture of $^{177}$Lu and $^{176}$Yb in an approximate mass ratio of $1:10^2$ to $1:10^{10}$, are used as base materials, wherein base materials that are insoluble in water, are converted into a soluble form, and wherein the method comprises the following steps:
  a) loading a first column (VS1) packed with cation exchange material, with the base materials solved in mineral acid and containing $^{177}$Lu and $^{176}$Yb in an approximate mass ratio of $1:10^2$ to $1:10^{10}$; exchanging the protons of the cation exchange material for ammonium ions, thereby using an NH$_4$Cl solution; and washing the cation exchange material of the first column (VS1) with water;
  b) linking the outlet of the first column (VS1) with the inlet of a second column (S1) that likewise is packed with a cation exchange material;
  c) applying a gradient of water and a chelating agent selected from the group consisting of: α-hydroxyisobutyrate [HIBA], citric acid, citrate, butyric acid, butyrate, EDTA, EGTA and ammonium ions, starting at 100% of H$_2$0 to 0.2 M of the chelating agent on the inlet of the first column (VS1), so as to elute $^{177}$Lu compounds from the first (VS1) and second column (S1);
  d) determining the radioactivity dose at the outlet of the second column (S1) in order to recognize the elution of $^{177}$Lu compounds; and collecting a first $^{177}$Lu eluate from the outlet of the second column (S1) in a vessel (F2); and protonating the chelating agent so as to inactivate same for the complex formation with $^{177}$Lu ions;
  e) loading a final column (S3) packed with a cation exchange material by continuously conveying the acidic $^{177}$Lu eluate of step d) to the inlet of the final column (S3); washing out the chelating agent with diluted mineral acid of lower concentration than approximately 0.1 M; removing traces of other metal ions from the $^{177}$Lu solution by washing the cation exchange material of the final column (S3) with mineral acid of various concentrations in a range of approximately 0.1 to 2.5 M; and
  f) eluting the $^{177}$Lu ions from the final column (S3) by way of a highly concentrated mineral acid of approximately 3 to 12 M; collecting the high purity $^{177}$Lu eluate in a vaporizer unit and removing the mineral acid by vaporization.

Due to promising clinical basic approaches in radionuclide therapy and radionuclide diagnostics there is an increasing worldwide demand for the reactor nuclide $^{177}$Lu. As a low-energetic β emitter with a comparatively short half life of T$_{1/2}$=6.71 days $^{177}$Lu constitutes an excellent vehicle for the specific deposition of large amounts of energy in small volumes. These physical properties for the most part are used in the form of radioimmuno-radionuclide therapy and peptide receptor radionuclide therapy in oncology, particularly for the treatment and diagnosis of tumors.

As is generally known, $^{177}$Lu may be produced by way of the subsequent nuclear reactions:

Nuclear reaction (1) constitutes a neutron capture reaction of $^{176}$Lu, which as a last consequence leads to carrier-added $^{177}$Lu ($^{177}$Lu carrier added [$^{177}$Lu c.a.]) and thus to limited product quality in the form of a significantly lower specific activity. As a result, in the marking of biomolecules with $^{177}$Lu, the activity bound per quantity of biomolecule is significantly lower. In a limited number of receptors on the surface of the tumor this leads to inferior therapy results or side effects. Through an irradiation of $^{176}$Lu the long-lasting metastable radionuclide $^{177m}$Lu (T½=160.1 d) is produced additionally, which is undesired in medicinal regards and with regard to radiation protection. Depending on the irradiation parameters, the portion of $^{177m}$Lu may be up to 0.1% of the $^{177}$Lu activity. With regard to the application on humans and in view of the high overall activities to be produced, such contamination is to be regarded critically. Within the scope of the treatments there is a persistent increased risk of releasing $^{177m}$Lu into the environment, which is due to a long half life of the nuclide and renal excretion of patients treated with Lu isotopes. Thus, the consumer in a hospital faces the problem of the safe handling and disposal of residual amounts of a long-fasting nuclide, which hardly is to be solved by the storage of radioactive waste customary in hospitals.

As was mentioned initially, carrier-added $^{177}$Lu, which currently is available on the market, has various disadvantages as opposed to non-carrier-added $^{177}$Lu. Due to its being more readily available so far, $^{177}$Lu c.a. nevertheless is preferred by many hospitals despite its disadvantages.

The $^{177}$Lu which currently is available on the market is essentially marketed by three suppliers. All suppliers produce $^{177}$Lu via the same route, i.e. directly from $^{176}$Lu via the above-indicated nuclear reaction (1).

This leads to the aforementioned problems.

A more attractive and medicinally and commercially more useful, but technically more demanding option thus is the production of non-carrier-added $^{177}$Lu via the indirect nuclear reaction (2). Such a nuclear reaction may be used, for example, on high-flux neutron sources in order to produce carrier-free $^{177}$Lu. Through irradiation with $^{176}$Yb the short-life radioisotope $^{177}$Yb (T½=1.9 h) is produced which disintegrates to $^{177}$Lu.

In this case the desired nuclide $^{177}$Lu is the nuclide of a different element than the element of the target nuclide $^{176}$Yb and therefore may be isolated chemically in a non-carrier-added form ($^{177}$Lu non carrier added [$^{177}$Lu n.c.a]), provided that a quantitative separation of Yb nuclides is possible. Since by the disintegration of the nuclide $^{177}$Yb no $^{177m}$Lu occurs, $^{177}$Lu of very high radioisomeric and radionuclidic purity may be produced.

A disadvantage in the choice of such a strategy, however, is the necessary radiochemical method for separating the Yb(macro)/$^{177}$Lu(micro) system. As the object nuclide and the target nuclide are two neighboring elements in the lanthanide group, the separation remains very demanding due to their chemical similarity.

An approach to the solution of the separation problem addressed above is to be found in the U.S. Pat. No. 6,716, 353 B1 which describes the separation of $^{177}$Lu n.c.a. from ytterbium using the indirect way in accordance with the above-indicated equation (2) in order to thus produce $^{177}$Lu with a high specific activity. In so doing, ytterbium, through the use of moderately concentrated mineral acids, initially is adsorbed by an LN resin which includes Di-(2-ethylhexyl) orthophosphoric acid (HDEHP) as extractant (Ln Resin of Eichrom). According to the method of U.S. Pat. No. 6,716, 353 B1, first ytterbium is eluted from an LN-resin containing chromatographic column using moderately concentrated hydrochloric acid, and subsequently $^{177}$Lu is obtained by using higher concentrated hydrochloric acid.

Due to the fact that microscopic amounts of $^{177}$Lu are to be separated from macroscopic amounts of ytterbium, a disadvantage of this prior art method is to be seen in that in accordance with U.S. Pat. No. 6,716,353 B1 first the macroscopic component is eluted of which an extreme surplus is present. Since spreading of the ytterbium by tailing at the end of a peak is a consequence of the extraction chromatographic system, the process is to be repeated several times in order to obtain a corresponding quality of $^{177}$Lu n.c.a., a residual amount of $^{176}$Yb not to be neglected on account of the system inevitably remaining in the Lu eluate. Moreover, in accordance with the prior art of U.S. Pat. No. 6,716,353 B1 merely activity amounts in a MBq range are obtained. The method disclosed in U.S. Pat. No. 6,716,353 B1 is an extraction chromatographic method, which means that an extractant is adsorbed on the surface of the column material that naturally in part is eluted with the desired $^{177}$Lu, thus additionally chemically contaminating the product. Moreover, for the elution of $^{177}$Lu a large amount of concentrated hydrochloric acid is required in which the product subsequently is present. Moreover, the method described in U.S. Pat. No. 6,716,353 B1 is very time-consuming and requires a process time of more than 16 hours on a single column. With the required repeating steps the production thus lasts several days.

Very high medicinal demands on the quality of the $^{177}$Lu nuclide thus render the manufacturing process and hence feasibility thereof more difficult.

However, a successful application of the radionuclide $^{177}$Lu is determined by the specific activity of the nuclide [Bq/mg] to be obtained through the production, as well as by the purity thereof. High specific activity of the radionuclide is required so as to achieve a specific activity that is as high as possible and thus optimally applied amounts of the corresponding radiopharmaceutical. In case no high specific activity and purity is achieved, this may lead inter alia to an adverse effect in the production of the radiopharmaceutical or to the quality of the radiopharmaceutical itself.

Based on the closest prior art of U.S. Pat. No. 6,716,353 B1 it therefore is an objectively technical object of the present invention of providing a method for making non-carrier-added high-purity $^{177}$Lu (non carrier added [n.c.a.] $^{177}$Lu) available on an industrial scale for medicinal purposes.

In particular, the invention relates to a method of manufacturing essentially non-carrier-added high purity $^{177}$Lu compounds for therapeutic and/or diagnostic purposes from $^{176}$Yb compounds irradiated with thermal neutrons, wherein the end products of neutron irradiation, which essentially contain a mixture of the nuclides $^{177}$Lu and $^{176}$Yb in an approximate mass ratio of $1:10^2$ to $1:10^{10}$, are used as base materials, wherein base materials that are insoluble in water, are converted into a soluble form possibly by way of mineral adds and/or increased temperature, and wherein the method comprises the following steps:

a) loading a first column packed with cation exchange material, with the base materials solved in mineral acid and containing $^{177}$Lu and $^{176}$Yb in an approximate mass ratio of $1:10^2$ to $1:10^{10}$; exchanging the protons of the cation exchange material for ammonium ions, thereby using an NH$_4$Cl solution; and washing the cation exchange material of the first column with water;

b) linking the outlet of the first column with the inlet of a second column that likewise is packed with a cation exchange material;

c) applying a gradient of water and a chelating agent selected from the group consisting of: α-hydroxyisobutyrate [HIBA], citric acid, citrate, butyric acid, butyrate, EDTA, EGTA and ammonium ions, starting at 100% of H$_2$0 to 0.2 M of the chelating agent on the inlet of the first column, so as to elute $^{177}$Lu compounds from the first and second column;

d) determining the radioactivity dose on the outlet of the second column in order to recognize the elution of $^{177}$Lu compounds; and collecting a first $^{177}$Lu eluate from the outlet of the second column in a vessel; and protonating the chelating agent so as to inactivate same for the complex formation with $^{177}$Lu ions;

e) loading a final column packed with a cation exchange material by continuously conveying the acidic $^{177}$Lu eluate of step d) to the inlet of the final column; washing out the chelating agent with diluted mineral acid of a concentration lower than approximately 0.1 M; removing traces of other metal ions from the $^{177}$Lu solution by washing the cation exchange material of the final column with mineral acid of various concentrations in a range of approximately 0.01 to 2.5 M; and f) eluting the $^{177}$Lu ions from the final column by way of a highly concentrated mineral acid of approximately 1M to 12M; collecting the high purity $^{177}$Lu eluate in a vaporizer unit and removing the mineral acid by vaporization.

The described embodiment may be repeated any number of times by repeating the separating method with α-hydroxyisobutyrate as chelating agent and the column systems described, as is described as an example in the following embodiment:

An alternative embodiment of the method in accordance with the invention is a method of manufacturing essentially non-carrier-added high-purity $^{177}$Lu compounds for medicinal purposes from $^{176}$Yb compounds irradiated with thermal neutrons, wherein the end products of neutron irradiation, which essentially contain a mixture of the nuclides $^{177}$Lu and $^{176}$Yb in an approximate mass ratio of $1:10^2$ to $1:10^{10}$, are used as base materials, wherein base materials that are insoluble in water, are converted into a soluble form by way of mineral acids and/or increased temperature, and wherein the method comprises the following steps:

a) loading a first column packed with cation exchange material, with the base materials solved in mineral acid and containing $^{177}$Lu and $^{176}$Yb in an approximate mass ratio of $1:10^2$ to $1:10^{10}$; exchanging the protons of the cation exchange material for ammonium ions, thereby using an NH$_4$Cl solution; and washing the cation exchange material of the first column with water;

b) linking the outlet of the first column with the inlet of a second column that likewise is packed with a cation exchange material;

c) applying a gradient of water and a chelating agent selected from the group consisting of: α-hydroxyisobutyrate [HIBA], citric acid, citrate, butyric acid, butyrate, EDTA, EGTA and ammonium ions, starting at 100% of $H_2O$ to 0.2 M of the chelating agent on the inlet of the first column;

d) determining the radioactivity dose on the outlet of the second column in order to recognize the elution of $^{177}$Lu compounds; and collecting a first $^{177}$Lu eluate from the outlet of the second column in a vessel; and protonating the chelating agent so as to inactivate same for the complex formation with $^{177}$Lu ions;

e) continuously conveying the acidic $^{177}$Lu eluate of step d) to the inlet of a third column packed with cation exchange material, the cation exchange material being present in protonated form due to the loading with acidic $^{177}$Lu eluate; exchanging the protons of the cation exchange material for ammonium ions, thereby using an $NH_4Cl$ solution; and washing the cation exchange material of the third column with water;

f) linking the outlet of the third column with the inlet of a fourth column packed with a cation exchange material;

g) applying a gradient of water and a chelating agent selected from the group consisting of: α-hydroxyisobutyrate [HIBA], citric acid, citrate, butyric acid, butyrate, EDTA, EGTA and ammonium ions, starting at 100% of $H_2O$ to 0.2 M of the chelating agent, on the inlet of the third column;

h) determining the radioactivity dose on the outlet of the fourth column in order to recognize the elution of $^{177}$Lu compounds; and collecting a second $^{177}$Lu eluate from the outlet of the fourth column in a vessel; and protonating the chelating agent so as to inactivate same for the complex formation with $^{177}$Lu ions;

i) loading a final column packed with a cation exchange material by continuously conveying the acidic $^{177}$Lu eluate of step h) to the inlet of the final column; washing out the chelating agent with diluted mineral acid; removing traces of other metal ions from the $^{177}$Lu solution by washing the cation exchange material of the final column with mineral acid of various concentrations in a range of approximately 0.01 to 2.5 M; and j) eluting the $^{177}$Lu ions from the final column by way of a concentrated mineral acid of approximately 1 M up to approximately 12M; collecting the high purity $^{177}$Lu eluate in a vaporizer unit and removing the mineral acid by vaporization.

Although the prior art in accordance with "Lehrbuch der Anorganischen Chemie" (textbook of inorganic chemistry) of Hollemann-Wieberg, Publishers Walter de Gruyter, Berlin-New York, 102$^{nd}$ edition, 2007, pages 1932 to 1933, has long disclosed the basic principle of separating lanthanides and particularly trivalent lanthanides on the basis of cation exchange and complexation, this merely holds for the existence of similar amounts of lanthanides and not for mass ratios in which the desired lanthanide cation of highest purity has to be isolated from a millionfold mass-related surplus of another lanthanide. Moreover, even from the prior art in accordance with Hollemann-Wieberg, particularly from FIG. 393, a merely insufficient selectivity between Lu and Yb is to be discerned, as both peaks significantly overlap upon performing elution of the lanthanides from the ion exchange resin Dowex-50 with ammonium α-hydroxyisobutyrate in a mixture of the lanthanides Eu, Gd, Tb, Dy, Ho, Er, Tm, Yb and Lu.

In contrast to the methods described in the prior art the present invention makes it possible for the first time to manufacture industrially relevant quantities of high-purity non-carrier-added $^{177}$Lu so that direct further processing such as, for example, coupling to biomolecules for the manufacture of radio-pharmaceuticals, may be performed. This is in particular due to the fact that the demands for purity and sterility on the obtained $^{177}$Lu product are given and that the method is fully compatible with EU-GMP guidelines.

A particular advantage of the manufacturing method in accordance with the present invention is that ytterbium may be processed in gram amounts. This makes the production of several terabecquerel (TBq) of $^{177}$Lu n.c.a. per production run possible. The manufacturing process thus for the first time enables the production of milligram amounts of the radionuclide $^{177}$Lu n.c.a. which, on account of its chemical and radiochemical purity, is suited for the use in nuclear medicine and diagnostics.

A further advantage of the method in accordance with the invention resides in that it can be performed within approximately 10 hours until the final product is obtained.

This is due to several factors. On the one hand, many processes run simultaneously and thus, through the pre-column systems VS1 and VS2 (cf. FIG. 1) used in a preferred embodiment, the processes of the respective subsequent separations may be started even while the previous separation is still running. Furthermore, the gradients of the pumps may be optimized to high separating factors and short retention times for $^{177}$Lu.

If e.g. pre-columns are used, for example, the loading of cation exchange material with acidic or acidified solutions which basically would not be optimally suited for separation, is enabled thereby. Thus, complex process steps such as vaporizing or neutralizing may be omitted at least to a great extent. Moreover, corrosion of the production plant is avoided in that no aggressive vapors occur through additional vaporizing steps. In addition, the risk of contamination is clearly reduced. By washing the pre-columns, contaminates can be removed from the system and, if need be, suitably be disposed of or recycled.

The use of pre-columns generally improves the separation of the desired $^{177}$Lu of Yb, and through a final purification step with a further column, the quality is further enhanced as even traces of other metals may be removed thereby from the $^{177}$Lu product. Moreover, the method in accordance with the invention enables the provision of an already sterile end product, which in addition is virtually free of toxins and which can be used directly for radio-pharmaceutical further processing, e.g. coupling to proteins.

The dimensioning of such pre-columns and separation columns with regard to their geometrical dimensions and the dimension ratios thereof among one another is well known to a person skilled in the art.

Preferably, the method in accordance with the invention is performed according to the following alternative embodiment: between steps d) and f) in accordance with claim 1 the following steps are performed additionally:

d.1) continuously conveying and at the same time acidifying the $^{177}$Lu eluate of step d) to the inlet of a third column packed with cation exchange material, the cation exchange material being present in protonated form due to the loading with acidic $^{177}$Lu eluate; exchanging the protons of the cation exchange material for ammonium ions, thereby using an $NH_4Cl$ solution; and washing the cation exchange material of the third column with water;

d.2) linking the outlet of the third column with the inlet of a fourth column packed with a cation exchange material;

d.3) applying a gradient of water and a chelating agent selected from the group consisting of: α-hydroxyisobutyrate [HIBA], citric acid, citrate, butyric acid, butyrate, EDTA, EGTA and ammonium ions, starting at 100% of $H_2O$ to 0.2 M of the chelating agent, on the inlet of the third column so as to elute $^{177}$Lu compounds from the third and fourth column;

d.4) determining the radioactivity dose on the outlet of the fourth column in order to recognize the elution of $^{177}$Lu compounds; and collecting a second $^{177}$Lu eluate from the outlet of the third column in a vessel; and protonating the chelating agent so as to inactivate same for the complex formation with $^{177}$Lu ions.

The advantage of such an approach resides in that with two pairs of columns respectively connected consecutively in a process direction, one pre-column and one separation column each are provided. After running through the second pair of pre-column and separation column the twofold purified $^{177}$Lu eluate is then given to a final separation column and is still liberated of further traces of metal. Furthermore, the concept of pre-columns/separation columns also has the advantage that a column application of acidic and acidified solutions, respectively, which in and for themselves would merely be partly suited for separation, is thereby made possible. The actual sharp separation is performed only in the separation column, i.e., for example, the second and/or fourth column. A further advantage is a reduced process time on account of quicker possible loading of the smaller pre-columns.

Of course, it is well known to a person skilled in the art that also more than two pairs of pre-columns/separation columns may be used, if need be.

With regard to recycling of the Yb materials used and of a reduced process time it is advantageous if after elution of the $^{177}$Lu compounds in steps d) and d.4) the first and second column and the third and fourth column are washed using higher concentrations of chelating agents so as to elute Yb ions from the cation exchange material, and Yb eluates obtained that essentially contain $^{176}$Yb ions, are collected separately for the purpose of re-using them as base material for the manufacture of $^{177}$Lu.

The following mineral acids for acidifying the $^{177}$Lu eluate have turned out to be suitable: $HNO_3$, HCl, $H_2SO_4$, HF, as well as organic acids such as, for example, acetic acid.

Provided that $^{177}$Lu compounds are to be gained from $^{176}$Yb oxides insoluble in water, it is possible and preferred to convert those oxides into a water-soluble form, e.g. by using 1M to 12M of $HNO_3$ or other oxidizing acids.

Typically, loading of the cation exchange materials is done using an acid concentration of 0.01 M to 2 M of $HNO_3$, HCl or other inorganic and/or organic acids.

A cation exchange material selected from the group consisting of: macroporous and gel-like cation exchange resins on a polystyrene basis or on the basis of other organic polymers as well as cation exchange resins on a silicate basis has turned out to be particularly suited.

Other than in the prior art preferably gram amounts of Yb base materials may be used and up to milligram amounts of $^{177}$Lu may be produced.

Typically, the yields are at several TBq of $^{177}$Lu and specific activities of approximately 3.9 TBq of $^{177}$Lu/mg of lutetium may be obtained, which are close to the theoretical physical limit of 4 TBq of $^{177}$Lu/mg of $^{177}$Lu.

For reasons of radiation protection as well as for reasons of pharmaceutical legislation the present method is performed in a hot cell of at least clean room class C in accordance with EU-GMP regulations.

In order to ensure the pharmaceutical quality of the non-carrier-added $^{177}$Lu product and obtain the manufacturing authorization, the chromatographic apparatus for performing the method in accordance with the invention was transferred to the environment of a clean room. Moreover, the use of a hot cell also makes it possible to perform the method in accordance with the invention in form of a semi-automatic or fully automatic process.

Finally, the method in accordance with the invention results in a non-carrier-added $^{177}$Lu compound ($^{177}$Lu n.c.a), the $^{177}$Lu compound being obtained according to at least one of the methods described herein.

A particular advantage of the non-carrier-added $^{177}$Lu compound is that it is suited directly for radiopharmaceutical use, i.e. without requiring further purification and/or sterilization.

With the $^{177}$Lu compound in accordance with the invention a marking ratio of more than 400 MBq of $^{177}$Lu per µg of peptide or polypeptide or other biomolecules may be reached.

A further advantage of the non-carrier-added $^{177}$Lu compound in accordance with the invention is that it may still be used for marking peptides, polypeptides, antibodies or other biomolecules even several weeks after their manufacture. This is particularly due to their high specific activity and their high radioisotopic and chemical purity.

With the method in accordance with the invention routine production of n.c.a. $^{177}$Lu in industrial amounts could be established for the first time.

Further advantages and features are to be seen from the description of an example and from the drawings:

In the following, the exemplary structure of an apparatus for performing the method in accordance with the invention is described, thereby referring to FIG. 1:

For reasons of radiation protection, the process is performed in an environment shielded by lead and/or plexiglass. This may be a hot cell or a different suitable system. In view of the fact that the product is used as pharmaceutical agent, the environment is to be classified into corresponding cleanliness classes in accordance with the demands of pharmaceutical manufacture (good manufacturing practice, GMP of the EU). In this case, the ambient condition in the hot cell has to conform to class C or higher.

The hot cell has suitable double door systems to the environment where auxiliary systems for production, such as HPLC pumps, syringe pumps or other conveying systems, and the control system are accommodated.

The system has several individual components such as chromatographic columns (VS1, S1, VS2, S2 and S3), flasks (F1 to F6) and pumps (P1 to P7) that are connected with each other via capillaries and valves.

Depending on their function, the pumps may be configured as vacuum pumps, syringe pumps, HPLC pumps, peristaltic pumps, or according to other principles of operation. In the present example, the pumps (P1) and (P2) are configured as HPLC pumps. They convey different concentrations (from 0.01 M to 10 M) and flow rates (from 0.05 ml/min to 100 ml/min) of $H_2O$, HIBA and $NH_4Cl$. The pumps (P3), (P4), (P5), (P6) convey different concentrations (from 0.01M to 10 M) and flow rates (from 0.05 ml/min to 100 ml/min) of further reagents such as HCl, $HNO_3$, $H_2O$ and air. In the preferred configuration, pumps P3 to P6 are syringe pumps or plunger pumps. However, they may be implemented by further valves to form a pump system in the configuration of a syringe pump. Pump 7 (P7) is a vacuum pump configured to be able to apply a variable negative pressure (from 1 mbar to 1000 mbar) to the system.

The components marked by (N2) (without numbers of their own) are inert gas sources, preferably nitrogen and argon, through which pressure of between 0.1 bar to 5 bar or even higher, depending on the configuration of the system, can be applied to the system.

Component (1) is configured for breaking ampoules and in addition for the conversion of an ytterbium oxide into ytterbium nitrate. In this example, the two separate functions are configured as integration of functions.

Component (2) is a vaporizer unit for drying up the lutetium solution. Component (3) is a system for accommodating the final product, such as, for example, a glass vial. Within the scope of an integration of functions, the components (2) and (3) can be configured as one structural component.

All valves in the example are depicted so as to be switchable in each direction. The position of the valves is selected so that the number thereof is minimized. As is obvious to a person of average skill from FIG. 1, other valve configurations, particularly for joining or separating functions, are easily conceivable.

Flasks (F1), (F2), (F3), (F4), (F5), (F6) are containers for receiving solutions. Preferred are flasks of glass having a volume adapted to the requirements of the method in accordance with the invention. Particularly for larger volumes the preferred embodiment is a plastic container.

The column system exemplarily shown in the preferred embodiment comprises so-called pre-columns (VS 1) and (VS 2) through which loading is carried out. The main columns (S1) and (S2) which in the example form the actual separation columns, are attached to the pre-columns, so that the respective partner columns (VS1) and (S1) or (VS2) and (S2) can be connected to a column system.

Figure 1:
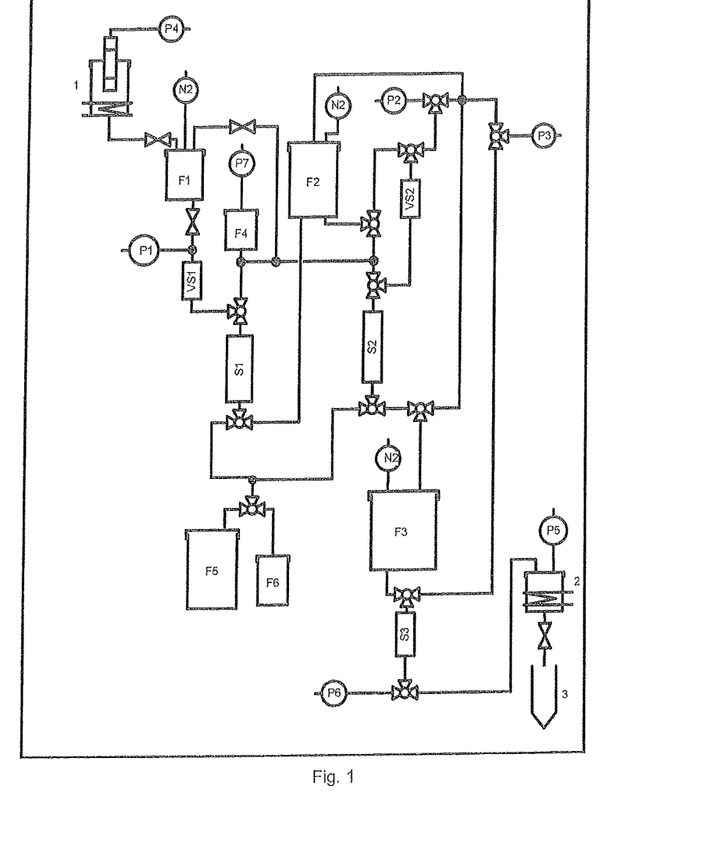
FIG. 1 shows a schematic structure of an exemplary apparatus for performing the method in accordance with the invention.

The entire fluid scheme of the exemplary apparatus for performing the invention is depicted in FIG. 1, irrespective of the actual configuration, also the configuration within hot cells. A preferred embodiment is the positioning of components (2) and (3) in a separate shielded device so as to enable the follow-up process, i.e. filling up the amounts of $^{177}Lu$ intended for the customer, all in one device. For logical reasons, the components (2) and (3) are integrated in one system. A further preferred embodiment is the location of component (3) in a separate shielded unit, so that the entire process takes place in one unit and merely the vial (3) for receiving the product is positioned in a pharmaceutically more sophisticated environment.

For control of the process, activity sensors are used in the example that each are positioned at the end of columns (S1), (S2) and (S3) in order to monitor the process of separation.

EXAMPLE

The present invention is a manufacturing process in which $^{177}Lu$ n.c.a. is extracted from reactor-irradiated $^{176}Yb$. For this purpose, the irradiated ampoule is opened in an ampoule cup and transferred into a conversion vessel (F1). The $^{176}Yb$ may be present as an insoluble oxide. For the extraction of the $^{177}Lu$ that occurred during irradiation, the base material has to be converted into a soluble form. In the present example, this may be achieved by the use of 1 M to 12 M of $HNO_3$, if need be, by heating.

Through the dilution to a lower acid concentration of between 0.01 M and 1.5 M of $HNO_3$ the solution can be loaded onto a pre-column system (VS1) as first column. By loading, the column material, a macroporous cation exchanger on a polystyrene basis, of the pre-column system is converted into a negative $H^+$ form (protonated form) for separation. Through the use of $NH_4Cl$ the column material of the pre-column system is converted into its $NH_4^+$ form. Subsequently, the pre-column system VS1 is washed with water and connected with the separation column S1 as second column.

Separation is conducted by way of the pump P1 at high flow rates (10-50 ml/min). For this purpose, a gradient of water and of α-hydroxy-isobutyrate (HIBA) used as chelating agent in the example, which is optimized for the separation in a VS1/S1 system, is set based on 100% of $H_2O$ to 0.2 M of HIBA and separation is run through the pre-column system VS1 and the separation column S1. The separation is monitored by way of dose rate sensors. As soon as the $^{177}Lu$ is eluted from the column S1, the eluate is collected in the collection flask F2.

Figure 2:
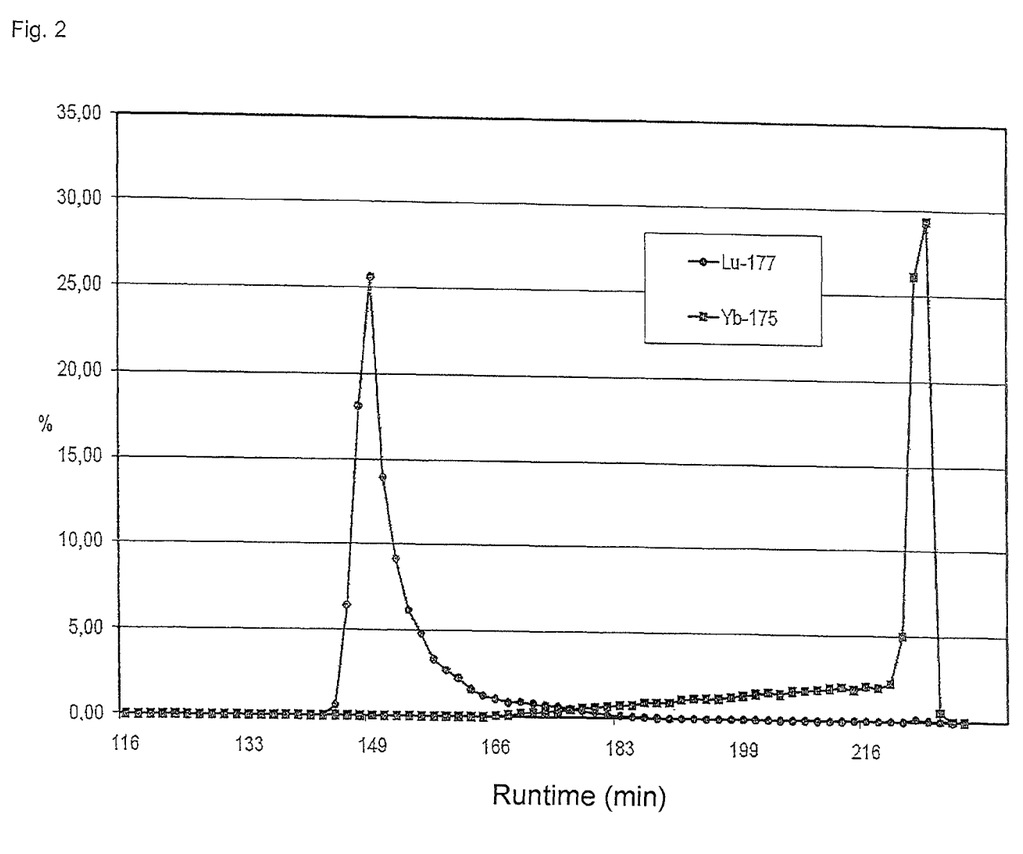
FIG. 2 shows a column chromatogram of the separation of $^{177}$Lu and ytterbium, recorded on the outlet of column S1 of FIG. 1.

The separation of $^{177}Lu$ and ytterbium is depicted as a chromatogram in FIG. 2. The ordinate indicates the eluted % amount of the $^{177}Lu$ and ytterbium, respectively, applied onto the column while the abscissa indicates the retention time in minutes. The massive peak rise of the ytterbium is due to the fact that shortly after a maximum of the lutetium peak a shift was made to a high concentration of HIBA, so that the ytterbium can be obtained within a reasonable time and in an acceptable volume.

The chelating agent still contained in the eluate of column S1, HIBA in the present example, is protonated through the addition of acid and thus is rendered inactive. After the $^{177}Lu$ has been collected, the ytterbium is eluted from the first and second column through the use of higher concentrated HIBA and collected separately for the purpose of recycling.

Through addition of an acid into F2 the eluate of S1 can be run on a second pre-column system VS2. In the example, the eluate is applied through nitrogen pressure to the pre-column system VS2 as third column still while further eluate is being collected. In so doing, the addition of an acid into the flask F2 is required either at regular intervals or continuously. In loading, the column material of the system VS2 likewise is converted into its $H^+$ form. For conversion of the undesired $H^+$ form into the $NH_4^+$ form preferred for the separation, the VS2 system is washed with $NH_4Cl$ and subsequently with water. The pre-column system VS2 is then connected with the separation column S2 as fourth column.

The further separation is conducted by way of an HPLC pump P2 at medium flow rates (1-10 ml/min). For this purpose, a gradient of water and HIBA optimized for separation in a VS2/S2 system as mentioned above is set and separation is run through the pre-column system VS2 and the separation column S2.

The separation is monitored by way of dose rate sensors. As soon as the $^{177}$Lu is eluted from the column S2, the eluate is collected in the collection flask F3. The chelating agent HIBA still contained in the eluate, is protonated through the addition of acid and thus is rendered inactive. After the $^{177}$Lu has been collected, the ytterbium is eluted from columns VS2 and S2 through the use of higher concentrated HIBA, and collected separately for the purpose of recycling.

Figure 3:
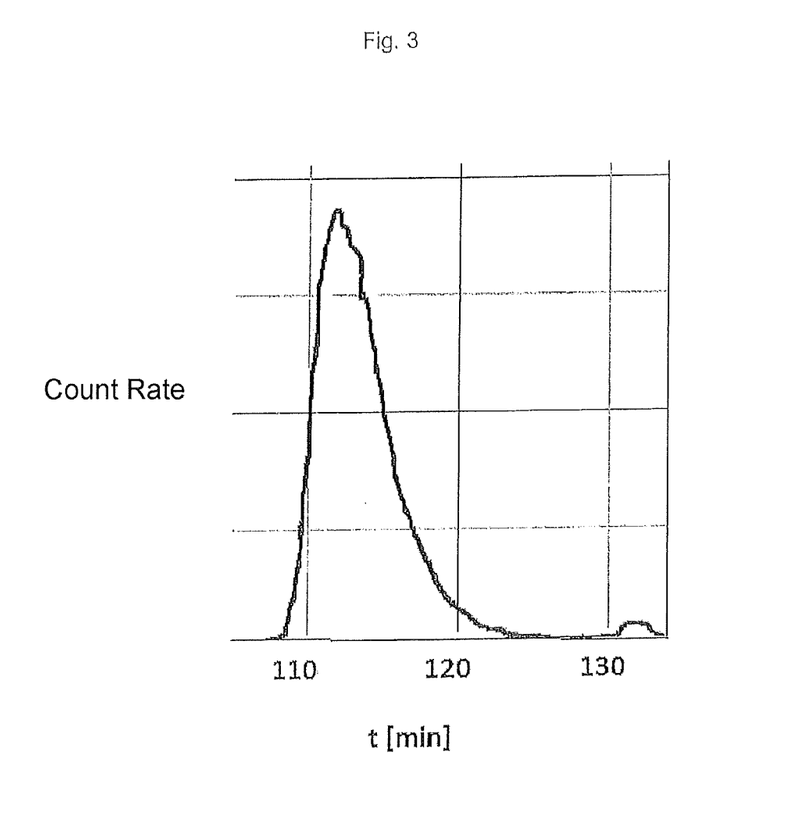
FIG. 3 shows a column chromatogram of the separation of $^{177}$Lu and ytterbium, recorded on the outlet of column S2 of FIG. 1.

FIG. 3 shows a section of a column chromatogram on column S2 in which again the dose rate is plotted against the retention time in minutes. Similar to FIG. 2 the ytterbium peak (now merely being very small) in FIG. 3 only appears to be shortly (with a retention time of approximately 135 min) after the lutetium peak as shortly after the maximum of the lutetium peak (approximately 115 min) a shift to a high concentration of HIBA was made. Otherwise, the ytterbium during the separation would appear only after several hours, which would unduly retard the process since it is, of course, useful to recycle the ytterbium, in particular $^{176}$Yb.

The eluate of column S2 is loaded from the collection flask F3 to a final column S3 as fifth column. For this purpose, while still being collected, the eluate is applied through nitrogen pressure from the collection flask F3 to column S3. In so doing, the addition of an acid into the flask F3 is required at regular intervals. After terminating loading of the final separation column S3, the column is liberated of HIBA by washing with diluted acid. Through selectively flushing the column S3 with acid of various concentrations a further separation of traces and impurities, respectively, of other metals is made possible.

After final purification on the column S3 the $^{177}$Lu is eluted into a vaporizer unit 2 by way of highly concentrated acid. The acid is removed through vaporization. The step also serves for sterilizing the end product at the same time.

The $^{177}$Lu n.c.a. can now be absorbed in the desired solvent and in the desired concentration. After a final determination of the activity obtained and quality check the produced $^{177}$Lu is filled into a vial 3 according to customer requirements.

Figure 4:
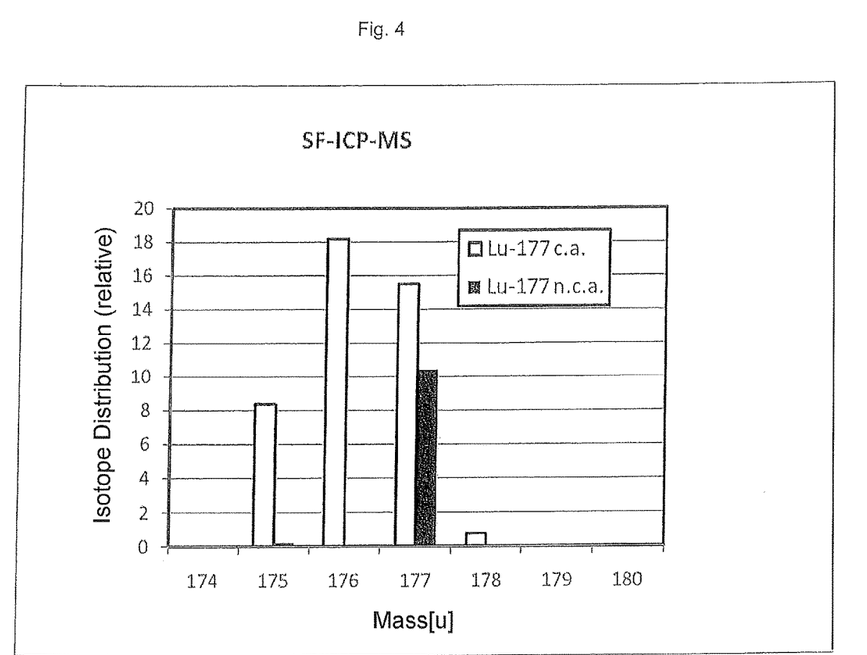
FIG. 4 shows an SF-ICP mass spectrum of the non-carrier-added $^{177}$Lu end product (n.c.a. $^{177}$Lu) obtained in accordance with the invention as compared to c.a. $^{177}$Lu in accordance with the prior art.

Typically, the non-carrier-added $^{177}$Lu compound obtained by way of the present method is characterized in that in a SF-ICP mass spectrum merely exhibits a peak at an atomic mass of 177, whereas c.a. $^{177}$Lu essentially exhibits three main peaks at atomic mass units of 175, 176 and 177. Such difference is shown in the mass spectrum of FIG. 4. The ordinate indicates the isotope distribution on a scale of relative frequency of 0 to 12. With the abscissa of FIG. 4 the atomic mass is indicated. The mass spectroscopic method used was the sector field mass spectrometry with inductively coupled plasma [Sector Field Inductively Coupled Plasma— Mass Spectrometry, SF-ICP-MS].

The invention claimed is:

1. A method of manufacturing non-carrier-added high-purity $^{177}$Lu compounds for medicinal purposes from $^{176}$Yb compounds irradiated with thermal neutrons, wherein the end products of neutron irradiation, which contain a mixture of $^{177}$Lu and $^{176}$Yb in a mass ratio of $1:10^2$ to $1:10^{10}$, are used as base materials, wherein base materials that are insoluble in water, are converted into a soluble form, and wherein the method comprises the following steps:
   a) loading a first column packed with cation exchange material, with the base materials dissolved in an acid selected from the group consisting of $HNO_3$, HCl, HF, $H_2SO_4$ and acetic acid; and containing $^{177}$Lu and $^{176}$Yb in a mass ratio of $1:10^2$ to $1:10^{10}$; exchanging the protons of the cation exchange material for ammonium ions, using an $NH_4Cl$ solution; and washing the cation exchange material of the first column with water;
   b) linking the outlet of the first column with the inlet of a second column that is packed with a cation exchange material;
   c) applying a gradient of water and a first chelating agent selected from the group consisting of: α-hydroxyisobutyrate, citric acid, citrate, butyric acid, butyrate, EDTA, EGTA and ammonium ions, starting at 100% of $H_2O$ to 0.2 M of the first chelating agent on the inlet of the first column, to elute $^{177}$Lu compounds from the first and second column;
   d) determining the radioactivity dose at the outlet of the second column in order to recognize the elution of $^{177}$Lu compounds; and collecting a first $^{177}$Lu eluate from the outlet of the second column in a vessel; and protonating the chelating agent to inactivate same for the complex formation with $^{177}$Lu ions;
   e) loading a final column packed with a cation exchange material by continuously conveying the first $^{177}$Lu eluate of step d) to the inlet of the final column; washing out the first chelating agent with diluted mineral acid of lower concentration than 0.1 M; removing traces of other metal ions from the first $^{177}$Lu solution by washing the cation exchange material of the final column with mineral acid of various concentrations in a range of 0.1 to 2.5 M; and
   f) eluting the $^{177}$Lu ions from the final column with a highly concentrated mineral acid of 3 to 12 M; collecting the high purity $^{177}$Lu eluate in a vaporizer unit and removing the mineral acid by vaporization.

2. The method in accordance with claim 1, characterized in that between steps d) and f) the following steps are performed:
   d.1) continuously conveying the first $^{177}$Lu eluate of step d) to the inlet of a third column packed with cation exchange material, the cation exchange material being present in protonated form due to the loading with the first $^{177}$Lu eluate; exchanging the protons of the cation exchange material for ammonium ions, using an $NH_4Cl$ solution; and washing the cation exchange material of the third column with water;
   d.2) linking the outlet of the third column with the inlet of a fourth column packed with a cation exchange material;
   d.3) applying a gradient of water and a second chelating agent selected from the group consisting of: α-hydroxyisobutyrate, citric acid, citrate, butyric acid, butyrate, EDTA, EGTA and ammonium ions, starting at 100% of $H_2O$ to 0.2 M of the second chelating agent, on the inlet of the third column to elute $^{177}$Lu compounds from the third and fourth column; and
   d.4) determining the radioactivity dose at the outlet of the fourth column in order to recognize the elution of $^{177}$Lu compounds; and collecting a second $^{177}$Lu eluate from the outlet of the third column in a vessel; and protonating the chelating agent to inactivate same for the complex formation with $^{177}$Lu ions.

3. The method in accordance with claim 2, characterized in that after elution of the $^{177}$Lu compounds in steps d) and d.4) the first and second column as well as the third and fourth column are washed using higher concentrations of chelating agents to elute Yb ions from the cation exchange material, and Yb eluates obtained that essentially contain $^{176}$Yb ions, are collected separately for the purpose of re-using them as base material for the manufacture of $^{177}$Lu.

4. The method in accordance with claim 1, characterized in that $^{176}$Yb oxides insoluble in water are converted into a water-soluble form by the use of 1 M to 12 M of $HNO_3$ or $H_2SO_4$.

5. The method in accordance with claim 1, characterized in that loading of the cation exchange materials is done using an acid concentration of 0.01 M to 2 M of $HNO_3$ or HCl.

6. The method in accordance with claim 1, characterized in that the cation exchange material is selected from the group consisting of: macroporous and gel-like polystyrene based cation exchange resins and silicate based cation exchange resins.

7. The method in accordance with claim 1, characterized in that gram amounts of base materials are used and milligram amounts of $^{177}$Lu are produced.

8. The method in accordance with claim 1, characterized in that yields of several TBq of $^{177}$Lu and specific activities of approximately 3.9 TBq of $^{177}$Lu per mg of lutetium are obtained.

9. The method in accordance with claim 1 wherein the use of cation exchange chromatography with a cation exchange resin as stationary phase and a chelating agent as mobile phase results in the manufacture of milligrams of high-purity, non-carrier-added $^{177}$Lu compounds from grams of $^{176}$Yb matrix.

10. A method of manufacturing non-carrier-added high purity $^{177}$Lu compounds for medicinal and/or diagnostic purposes from $^{176}$Yb compounds irradiated with thermal neutrons, wherein the end products of neutron irradiation, which essentially contain a mixture of $^{177}$Lu and $^{176}$Yb in a mass ratio of $1:10^2$ to $1:10^{10}$, are used as base materials, wherein base materials that are insoluble in water, are converted into a soluble form, and wherein the method comprises the following steps:

a) loading a first column packed with cation exchange material, with the base materials dissolved in an acid selected from the group consisting of $HNO_3$, HCl, HF, $H_2SO_4$ and acetic acid; and containing $^{177}$Lu and $^{176}$Yb in a mass ratio of $1:10^2$ to $1:10^{10}$; exchanging the protons of the cation exchange material for ammonium ions, using an $NH_4Cl$ solution; and washing the cation exchange material of the first column with water;

b) linking the outlet of the first column with the inlet of a second column that is packed with a cation exchange material;

c) applying a gradient of water and a chelating agent selected from the group consisting of: α-hydroxyisobutyrate, citric acid, citrate, butyric acid, butyrate, EDTA, EGTA and ammonium ions, starting at 100% of $H_2O$ to 0.2 M of the chelating agent on the inlet of the first column;

d) determining the radioactivity dose at the outlet of the second column in order to recognize the elution of $^{177}$Lu compounds; and collecting a first $^{177}$Lu eluate from the outlet of the second column in a vessel; and protonating the chelating agent to inactivate same for the complex formation with $^{177}$Lu ions;

e) continuously conveying the first $^{177}$Lu eluate of step d) to the inlet of a third column packed with cation exchange material, the cation exchange material being present in protonated form due to the loading with the first $^{177}$Lu eluate; exchanging the protons of the cation exchange material for ammonium ions, using an $NH_4Cl$ solution; and washing the cation exchange material of the third column with water;

f) linking the outlet of the third column with the inlet of a fourth column packed with a cation exchange material;

g) applying a gradient of water and a chelating agent selected from the group consisting of: α-hydroxyisobutyrate, citric acid, citrate, butyric acid, butyrate, EDTA, EGTA and ammonium ions, starting at 100% of $H_2O$ to 0.2 M of the chelating agent, on the inlet of the third column;

h) determining the radioactivity dose at the outlet of the fourth column in order to recognize the elution of $^{177}$Lu compounds; and collecting a second $^{177}$Lu eluate from the outlet of the fourth column in a vessel; and protonating the chelating agent to inactivate same for the complex formation with $^{177}$Lu ions;

i) loading a fifth column packed with a cation exchange material by continuously conveying the acidic $^{177}$Lu eluate of step h) to the inlet of the fifth column; washing out the chelating agent with diluted mineral acid; removing traces of other metal ions from the $^{177}$Lu solution by washing the cation exchange material of the fifth column with mineral acid of various concentrations in a range of 0.01 to 2.5 M; and j) eluting the $^{177}$Lu ions from the fifth column with concentrated mineral acid of 3 M up to 12 M; collecting the high purity $^{177}$Lu eluate in a vaporizer unit and removing the mineral acid by vaporization.

11. The method in accordance with claim 10 wherein the use of cation exchange chromatography with a cation exchange resin as stationary phase and a chelating agent as mobile phase results in the manufacture of milligrams of high-purity, non-carrier-added $^{177}$Lu compounds from grams of $^{176}$Yb matrix.

* * * * *